United States Patent [19]

Hayao et al.

[11] 4,006,232

[45] Feb. 1, 1977

[54] THERAPEUTIC METHOD OF TREATING CARDIAC ARRHYTHMIAS UTILIZING 3-SUBSTITUTED DIPHENYLHYDANTOINS

[75] Inventors: Shin Hayao, Tokyo, Japan; Herbert John Havera, Edwardsburg, Mich.; Wallace Glenn Strycker, Goshen, Ind.

[73] Assignee: Miles Laboratories, Inc., Elkhart, Ind.

[22] Filed: Nov. 15, 1974

[21] Appl. No.: 524,297

Related U.S. Application Data

[62] Division of Ser. No. 381,021, July 20, 1973, Pat. No. 3,892,748.

[52] U.S. Cl. .................................. 424/250; 424/263; 424/267; 424/273

[51] Int. Cl.[2] ...................................... A61K 31/495

[58] Field of Search .................. 424/250, 263, 267; 260/268 PH, 293.7, 293.66, 295 SP, 295 D, 295 L, 309.5

[56] References Cited

UNITED STATES PATENTS 3,892,748 7/1975 Hayao et al. ................ 260/268 PH

OTHER PUBLICATIONS

Chemical Abstracts 55:21100*a* (1961).

Chemical Abstracts 70:37780*a* (1969).

*Primary Examiner*—Leonard Schenkman

*Attorney, Agent, or Firm*—Myron B. Sokolowski

[57] ABSTRACT

3-substituted-5,5-diphenylhydantoin derivatives in which the 5,5-diphenylhydantoin moiety is attached at $C_3$ by a loweralkylene bridge to a 4-phenyl-1-piperidyl, 4-hydroxy-4-phenyl-1-piperidyl, 4-phenyl-1,2,3,6-tetrahydropyridyl, 4-phenyl-1-piperazinyl, or loweralkylamino group are useful in the treatment of cardiac arrhythmias in mammals. One or both of the 5,5-diphenyl substituents optionally can be substituted in the ortho-, meta-, or para-positions with halogeno, loweralkyl, loweralkoxy, amino or nitro groups.

17 Claims, No Drawings

THERAPEUTIC METHOD OF TREATING CARDIAC ARRHYTHMIAS UTILIZING 3-SUBSTITUTED DIPHENYLHYDANTOINS

This is a division, of application Ser. No. 381,021, filed July 20, 1973, now U.S. Pat. No. 3,892,748.

BACKGROUND OF THE INVENTION

1. Field of the Invention

Cardiac arrhythmias are disorders of impulse generation in the mammalian heart. Although the physiological mechanisms of these disorders are not completely understood, they are believed to result from disruptions of normal cardiac pacemaker activity, disturbances in the cardiac conductive fibers, or a combination of the former and latter factors. Caridac arrhythmias of clinical significance in man include: (A) premature contractions (extra -systoles) having their origin in abnormal focal points in the atria or ventricles, (B) paroxysmal supraventricular tachycardia, (C) atrial flutter, (D) atrial fibrillation, (E) ventricular tachycardia, and (F) ventricular fibrillation. These arrhythmias can be induced in experimental animals to study physiological mechanisms involved in such arrhythmias or to screen new antiarrhythmic agents.

Arrhythmias are treated clinically by administration of a variety of drugs, although quinidine and procainamide are current mainstays. Quinidine is the d-isomer of quinine while procainamide is p-amino N-(2-diethylamino-ethyl)-benzamide. Both drugs require extreme care in administration and are considered relatively dangerous. In weighing their efficacy over their danger, however, the former is countervailing. Because of such limitations in currently available antiarrhythmic drugs, there have been efforts to discover safer substitutes. The discovery of the antiarrhythmic activity of hydantoin opened new approaches in the design of new compounds exhibiting such activity. For a general discussion of this field, to which the instant invention pertains, refer to — G. K. Moe and J. A. Albildskov, "Antiarrhythmic Drugs," in: *The Pharmacological Basis of Therapeutics*, L. S. Goodman and A. Gilman, Editors, 4th Edition, The MacMillan Company, New York, Chapter 32 (1970).

2. Description of the Prior Art

U.S. Pat. No. 2,409,754 (1954) discloses the synthesis and structures of diphenylhydantoin, or 5,5-diphenyl-2,4-imidazolidinedione, which is represented by Formula I:

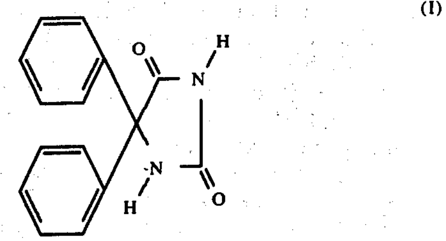

Diphenylhydantoin (hereafter referred to as DPH) was utilized initially in the treatment of epilepsy, but was discovered later to have important antiarrhythmic applications. Of particular interest to scientists and clinicians was that the pharmacodynamics of DPH differed from quinidine and procainamide, and that DPH did not exhibit the dangerous properties of its precursors. DPH was found specifically to antagonize ventricular arrhythmias induced by digitalis. In its action on the heart, DPH depresses ventricular automaticity, enhances artio-ventricular nodal conduction, and reduces the effective refractory period. DPH, however, is not without untoward side effects: dizziness, nausea, emesis, nystigmus, and ataxia. Large doses may produce atrio-ventricular blockage, bradycardia, or even cardiac arrest. For a review of the current status of DPH as an antiarrhythmic agent, see — L. S. Dreifus and Y. Watanabe, Amer. Heart J., 80: 709–713 (1970).

There have been several attempts to improve the activity and to eliminate the side effects of DPH. Henze and Isbell (J. Amer. Chem. Soc., 76: 4152-4156 [1954] described twelve 5-(substituted-phenyl)- and 5,5-di(-substituted-phenyl)-hydantoins. Of these compounds, only 5-(4-aminophenyl)-5-phenylhydantoin displayed activity, but only to the extent of 50% of DPH.

W. Chiti and P. Chiarini (11. Farmaco, Sci. Ed., 13: 579–589 [1958]) synthesized seventeen derivatives of DPH, the following three of which are representative:

A. 3-(3-diethylaminopropyl)-5,5-diphenylhydantoin,

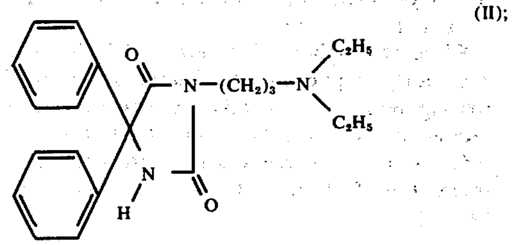

B. 3-[3(1-piperidyl)propyl]-5,5-diphenylhydantoin,

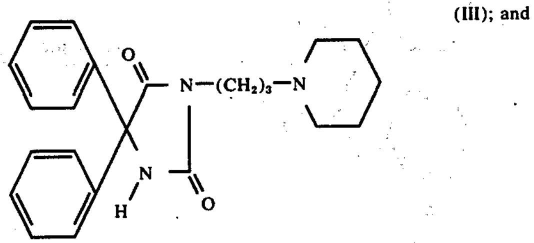

C. 3-(3-morpholinopropyl)-5,5-diphenylhydantoin,

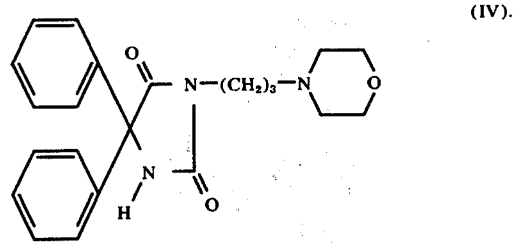

Chiti and Chiarini did not disclose whether any of their seventeen compounds exhibited antiarrhythmic activity.

The compounds of this invention are more effective in antiarrhythmic activity and cause less cardiac depression than DPH or derivatives II, III, and IV.

SUMMARY

This invention relates to compounds of the formula

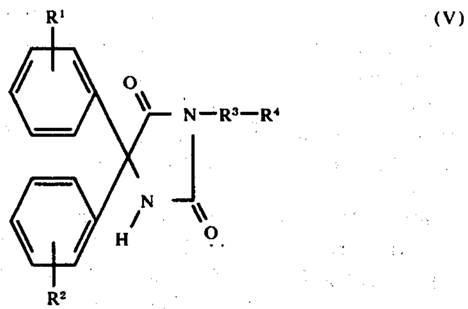

and pharmacologically acceptable, nontoxic acid addition salts thereof. The symbols $R^1$, $R^2$, $R^3$, and $R^4$ in Formula V are defined as follows:

$R^1$ and $R^2$ may be hydrogen, halogeno, loweralkyl of 1 to 3 carbon atoms, loweralkoxy of 1 to 3 carbon atoms, amino, or nitro, and may be located at the ortho-, meta-, or para-position of the phenyl moieties;

$R^3$ may be methylene, ethylene, trimethylene, 2-hydroxy-trimethylene, tetramethylene, or 2-hydroxy-tetramethylene; and $R^4$ may be 4-phenyl-1-piperidyl, 4-hydroxy-4-phenyl-1-piperidyl, 4-phenyl-1,2,3,6-tetrahydropyridyl, 4-phenyl-1-piperazinyl, loweralkyl amino of 1 to 4 carbon atoms, and diloweralkylamino of 2 to 8 carbon atoms.

Compounds represented by V are synthesized by the method of Hoffmann (Bull. Soc. Chim., pp 15–17 [1950]):

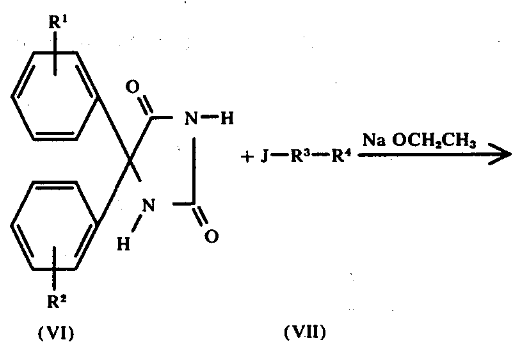

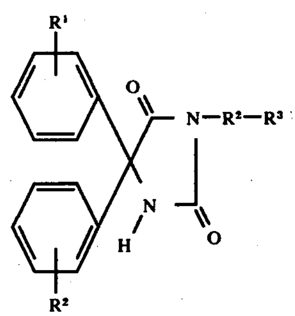

In VI and VII, $R^1$, $R^2$, $R^3$, and $R^4$ have the same meaning as defined in V, and J is either chlorine or bromine.

The starting material, VI, is prepared according to the method disclosed by H. Henze and A. Isbell (J. Am. Chem. Soc., 76: 4152–4156 [1954]) or by the synthesis described by J. Melton and H. Henze (J. Am. Chem. Soc., 69: 2018–2020 [1947]) Compounds represented by VII are prepared by methods well known in organic chemistry.

An alternate synthesis involves: (1) reaction of a substituted amine, VIII, to form a corresponding derivative of urea, IX; and (2) reaction of the urea derivative, IX, with benzil or substituted-benzil, X:

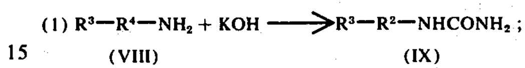

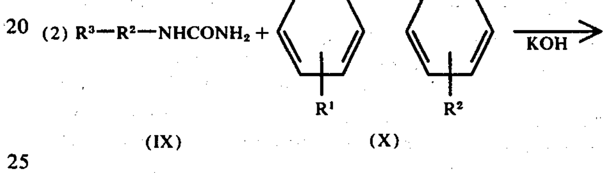

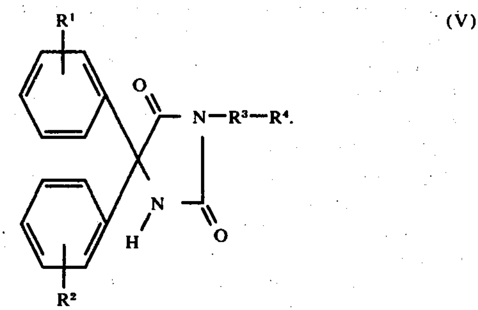

Details of this alternate synthesis and the starting materials VIII and X are described by H. Hatt et al. (J. Chem. Soc., pp 93–96 [1936]) and by W. Dunnavant and F. James (J. Am. Chem. Soc., 78: 2740–2743 [1956]).

Pharmacologically acceptable, nontoxic acid addition salts of V are prepared by standard methods. Preferably hydrochloric, maleic, or oxalic acids are utilized.

The following compounds are representative of V:

1. 3-[3-(4-phenyl-1-piperazinyl)propyl]-5,5-diphenylhydantoin maleate (MA 1586);
2. 3-[3-(4-phenyl-1-piperidyl)propyl]-5,5-diphenylhydantoin (MA 1598);
3. 3-[2-(4-phenyl-1-piperidyl)ethyl]-5,5-diphenylhydantoin hydrochloride (TR 2906);
4. 5,5-diphenyl-3-[2-(4-phenyl-1,2,3,6-tetrahydropyridyl) ethyl]hydantoin hydrochloride (TR 2913);
5. 5,5-diphenyl-3-[3-(4-hydroxy-4-phenyl-1-piperidyl) propyl]hydantoin hydrochloride (TR 2916);
6. 3-(3-t-butylamino-2-hydroxypropyl)-5,5-diphenylhydantoin hydrochloride (TR 2921);
7. 5,5-diphenyl-3-[2-(4-hydroxy-4-phenyl-1-piperidyl) ethyl]hydantoin hydrochloride (TR 2951);
8. 3-[3-(4-phenyl-1-piperidyl)propyl]-5,5-di(4-chlorophenyl)hydantoin hydrochloride (TR 2984);
9. 3-[3-(4-phenyl-1-piperidyl)propyl]-5-(4-methoxyphenyl)-5-phenylhydantoin hydrochloride (TR 2986);

10. 3-[3-(4-phenyl-1-piperidyl)propyl]-5,5-di(4-methoxyphenyl)hydantoin hydrochloride (TR 2986);
11. 3-[3-(4-phenyl-1-piperidyl)propyl]-5-(4-bromophenyl)-5-phenylhydantoin hydrochloride (TR 2987);
12 3-[3-(4-phenyl-1-piperidyl)propyl]-5-phenyl-5-(4-tolyl)hydantoin maleate (TR 2993);
13. 3-[3-(4-phenyl-1-piperidyl)propyl]-5,5-di(4-tolyl)-hydantoin (TR 3001);
14. 3-[3-(4-phenyl-1-piperidyl)propyl]-5-(4-nitrophenyl)-5-phenylhydantoin (TR 3012);
15. 3-[3-(4-phenyl-1-piperidyl)propyl]-5-(4-aminophenyl)-5-phenylhydantoin (TR 3021);
16. 5,5-diphenyl-3-[2-hydroxy-3-(4-phenyl-1-piperidyl)propyl]-hydantoin oxalate (TR 3104);
17. 5,5-di-(4-tolyl)-3-[2-hydroxy-3-(t-butylamino)-propyl]-hydantoin hemioxalate (TR 3130); and
18. 3-[3-(4-hydroxy-4-phenyl-1-piperidyl)propyl]-5,5-di-(4-tolyl)hydantoin (TR 3163).

Compounds having formula V are more effective for the treatment of cardiac arrhythmias and cause considerably less cardiac depression than diphenylhydantoin or the prior art diphenylhydantoin derivatives II, III, and IV (Cf. "Description of the Prior Art", above). Details of the pharmacology of the compounds listed above are found in Examples 19 and 20 in the following section, "Description of the Preferred Embodiments".

This invention also pertains to a method of treating a human or other mammal having a cardiac arrhythmia which comprises administering to said human or other mammal an effective amount of a compound of formula V or a nontoxic pharmacologically acceptable acid solution salt thereof. Said compounds may be administered orally, rectally, intravenously, parenterally, intramuscularly, intraperitoneally or by other routes of administration. By an "effective amount" is meant a dose which is required to correct the arrhythmia to normal or near-normal cardiac rhythm and to maintain such rhythm. This amount may range from 5 to 500 mg per day, depending on the severity of the cardiac arrhythmia and upon the weight of the human or other mammal to whom or which the compounds are administered.

DESCRIPTION OF THE PREFERRED EMBODIMENTS

EXAMPLE 1

3-[3-(4-phenyl-1-piperazinyl)propyl]-5,5-diphenylhydantoin maleate (MA 1856).

5,5-diphenylhydantoin, 25.2 g (0.1 mole), was added to a solution of 2.3 g (0.1 mole) of sodium in 300 ml of anhydrous ethanol and the suspension was heated under reflux for half an hour. 4-phenyl-1-(3-chloropropyl)piperazine, (23.9 g, 0.1 mole) slowly was added to the suspension and the mixture was heated under reflux with stirring for 16 hours. The solvent was removed in vacuo, the concentrate was suspended in water, and the free base was extracted with chloroform. The dried extracts were concentrated in vacuo to an oil. The oil was dissolved in hot methanol and 14 g (0.12 mole) of maleic acid was added. The hot solution was filtered and the filtrate was cooled. The resulting solid was collected and recrystallized from an aqueous-methanol solution.

Yield: 32 g (56.2%); m.p., 212°–213.5° (dec.).

Calculated for $C_{28}H_{30}N_4O_2 \cdot C_4H_4O_4$: C, 67.37; H, 5.96; N, 9.82. Found: C, 67.85; H, 6.28; N, 9.90.

EXAMPLE 2

Preparation of 3-[3-(4-phenyl-1-piperidyl)propyl]-5,5-diphenylhydantoin (MA 1598).

25.2 g (0.1 mole) of 5,5-diphenylhydantoin was added to a solution of 2.3 g (0.1 mole) of sodium in 350 ml of anhydrous ethanol, and the suspension was heated under reflux with stirring for half an hour. 4-phenyl-1-(3-chloropropyl piperidine, 23.8 g (0.1 mole) was added, and the mixture was heated under reflux with stirring for 18 hours. The solvent was removed in vacuo and the concentrate was suspended in water and extracted with chloroform. The dried extracts were concentrated in vacuo to a solid. The solid was recrystallised from an aqueous-methanol-DMF solution.

Yield: 38 g (84%); m.p., 162°–163°.

Calculated for $C_{29}H_{31}N_3O_2$: N, 9.27. Found: N, 9.30.

A mixture of the free base (38 g, 0.084 mole) and maleic acid (0.1 mole) was dissolved in hot methanol water, filtered and cooled. The resulting solid was collected and recrystallized from an aqueous-methanol solution.

Yield: 30.7 g (64.3%); m.p., 223.5–224.5° (dec.).

Calculated for $C_{29}H_{31}N_3O_2 \cdot C_4H_4O_4$: C, 69.60; H, 6.15; N, 7.38. Found: C, 69.31; H, 6.18; N, 7.57.

EXAMPLE 3

3-[2-(4-phenyl-1-piperidyl)ethyl]-5,5-diphenylhydantoin hydrochloride (TR 2906).

5,5-diphenylhydantoin (12.5 g, 0.05 mole) was added to sodium ethoxide (0.1 mole) in 350 ml of anhydrous ethanol. The mixture was heated to boiling and 1-(2-chloroethyl)-4-phenylpiperidine · HCl (13 g, 0.05 mole) was added. The mixture was refluxed with stirring for 16 hours, filtered, and diluted with $H_2O$ to form a white solid.

Yield: 11.5 g (52.3%); m.p., 175–7°.

Calculated for $C_{28}H_{29}N_3O_2$: C, 76.52; H, 6.65; N, 9.56. Found: C, 76.00; H, 6.72; N, 9.25.

The free base (11.5 g, 0.026 mole) was converted to the HCl salt with HClg/2-propanol. concentrated and crsytallized in acetone. The solid was recrystallized twice from 2-propanol-ether and again from methanol-ether.

Yield: 6.5 g (52%); m.p., 193°–4° (dec.).

Calculated for $C_{28}H_{29}N_3O_2 \cdot HCl$: C, 70.65; H, 6.34; N, 8.82. Found: C, 71.31; H, 6.23; N, 8.82.

EXAMPLE 4

5,5-diphenyl-3-[2-(4-phenyl-1,2,3,6-tetrahydropyridyl)ethyl]hydantoin hydrochloride (TR 2913).

5,5-diphenylhydantoin (12.5 g, 0.05 mole) was added to sodium ethoxide (0.1 mole) in 350 ml of anhydrous ethanol. The mixture was heated to boiling and 1-(2-chloroethyl)-4-phenyl-1,2,3,6-tetrahydropyridine · HBr (16 g, 0.05 mole) was added. The mixture was refluxed with stirring for 16 hours, filtered and diluted with $H_2O$ to form a white solid.

Yield: 14 g (64%); m.p., 211°–3°.

Calculated for $C_{28}H_{29}N_3O_2$: C, 76.82; H, 6.22; N, 9.61. Found: C, 77.12; H, 6.32; N, 9.34.

The free base (10 g, 0.032 mole) was converted to the hydrochloride salt with methanol and Hclg/2-propanol, filtered and diluted with ethylacetate.

Yield: 7.3 g (48.2%); m.p., 230°–2° (dec.).

Calculated for $C_{28}H_{27}N_3O_2 \cdot HCl$: C, 70.95; H, 5.95; N, 8.86. Found: C, 70.96; H, 5.98; N, 8.78.

EXAMPLE 5

5,5-diphenyl-3-[3-(4-hydroxy-4-phenyl-1-piperidyl)-propyl]hydantoin hydrochloride (TR 2916).

A. N-3(4-hydroxy-4-phenyl-1-piperidyl)propyl urea. KOH (5.6 g) and KCNO (8.1 g) in $H_2O$ were added to a solution of 1 (3-aminopropyl)-4-hydroxy-4-phenylpiperidine · 2HCl (30.7 g, 0.1 mole) in $H_2O$. The mixture was stirred for an hour and concentrated in vacuo to dryness. The solid was recrystallized from 2-propanol-Skelly "B". Yield: 10 g, (36%); m.p., 162°–3°.

Calculated for $C_{15}H_{23}N_3O_2$: C, 65.00; H, 8.30; N, 15.16. Found: C, 64.86; H, 8.51; N, 14.86.

B. A mixture of N-3-(4-hydroxy-4-phenyl-1-piperidyl)propyl urea (10 g, 0.036 mole), benzil (3.8 g, 0.018 mole), 50 ml of ethanol and 11 cc of 66% KOH was warmed to form a solution and let stand at room temperature for 1 hour. The solution was acidified with conc. HCl and concentrated. The concentrate was dissolved in hot aqueous ethanol, filtered and basified with dilute $Na_2CO_3$ solution. The crude solid was recrystallized from aqueous MeOH.

Yield: 7 g (41%); m.p., 174°–5°.

Calculated for $C_{29}H_{31}N_3O_3$: C, 74.18; H, 6.64; N, 8.95. Found: C, 75.68; H, 6.70; N, 8.96.

The free base (7 g, 0.015 mole) was converted to the HCl salt with HCl/2-propanol-ethylacetate and recrystallized from ethanol-ether.

Yield: 6.5 g (86%); m.p., 213°–4° (dec.).

Calculated for $C_{29}H_{31}N_3O_3 \cdot HCl$: C, 68.83; H, 6.36; N, 8.30. Found: C, 68.92; H, 6.38; N, 8.30.

EXAMPLE 6

3-(3-t-butylamino-2-hydroxypropyl)-5,5-diphenyl-hydantoin hydrochloride (TR 2921).

5,5-diphenylhydantoin (12.6 g, 0.05 mole) was added to sodium ethoxide (0.05 mole) in hot anhydrous ethanol. Epichlorohydrin (6 g) was added to this hot solution and the mixture was refluxed for 3 hours, concentrated and diluted with $H_2O$. The mixture was extracted with $CHCl_3$ and the extracts were dried ($MgSo_4$) and concentrated to dryness. The concentrate and 40 ml of t-$BuNH_2$ in methanol were refluxed for 2 hours and concentrated to dryness. The concentrate was crystallized from benzene-Skelly "B" and recrystallized from benzene.

Yield: 10 g (52.5%); m.p., 159°–160°.

Calculated for $C_{22}H_{27}N_3O_2$: C, 69.27; H, 7.13. Found: C, 69.76; H, 7.32.

The free base (10 g, 0.026 mole) was converted to the HCl salt with HClg/2-propanol and the solid was recrystallized from methanol-ethylacetate.

Yield: 6.5 g, (59.6%); m.p., 281°–3° (dec.).

Calculated for $C_{22}H_{27}N_3O_3 \cdot HCl$: C, 63.20; H, 6.75; N, 10.05. Found: C, 63.34; H, 6.69; N, 10.16.

EXAMPLE 7

5,5-diphenyl-3-[2-(4-hydroxy-4-phenyl-1-piperidyl)ethyl]hydantoin hydrochloride (TR 2921).

Conc. HCl (6.5 g) was added to 1-(2-aminoethyl)-4-hydroxy-4-phenylpiperidine (13.4 g, 0.076 mole) and KCNO (6 g, 0.074 mole) in a small amount of $H_2O$. The mixture was stirred for 1 hour and concentrated to dryness. The concentrate was boiled in anhydrous ethanol for 1 hour and concentrated to dryness: $\nu_{max}^{CHCl}$ 1670 cm. The concentrate and benzil (7.6 g) in 100 ml of ethanol were treated with 22 ml of 66% KOH and stirred at room temperature for 2 hours. The solution was acidified with conc. HCl and the solid was dissolved by addition of warm aqueous methanol. The solution was made basic with dilute $NaHCO_3$ and the solid was collected and recrystallized from aqueous dimethylformamide-methanol and again from aqueous-Dioxane.

Yield: 11 g (31.8%); m.p., 214°–5°.

Calculated for $C_{28}H_{29}N_3O_3$; C, 73.83; H, 6.41; N, 9.22. Found: C, 74.14; H, 6.52; N, 9.30.

The free base (10 g, 0.022 mole) in methanol-ethylacetate was converted to the HCl salt with $HCl_g$/2-propanol and ether. The salt was recrystallized from 2-propanolmethanol-ether.

Yield: 6.6 g (61%); m.p., 241°–2° (dec.).

Calculated for $C_{28}H_{29}N_3O_3 \cdot HCl$: C, 68.36; H, 6.15; H, 8.54. Found: C, 68.41; H, 6.18; N, 8.47.

EXAMPLE 8

3-[3-(4-phenyl-1-piperidyl)propyl]-5,5-di(4-chlorophenyl)hydantoin hydrochloride (TR 2984).

5,5-di(4-chlorophenyl)hydantoin (8 g, 0.025 mole) was added to sodium ethoxide (0.05 mole) in 300 ml of warm anhydrous ethanol. 1-(3-chloropropyl)-4-phenylpiperidine · HCl (6.8 g, 0.025 mole) was added and the mixture was refluxed with stirring for 18 hours, filtered and diluted with $H_2O$. The solid was recrystallized from aqueous methanol-dimethylformamide and again from aqueous ethanol.

Yield: 10.0 g (76.5%); m.p., 191°–2°.

Calculated for $C_{29}H_{20}Cl_2N_3O_2$: C, 66.67; H, 5.60; N, 8.04. Found: C, 66.46; H, 5.60; N, 7.96.

The free base (10 g, 0.019 mole) in hot anhydrous ethanol was converted to the HCl salt with HCl/2-propanol and ether. The salt wad recrystallized from 2-propanolmethanol-ether.

Yield: 9.5 g (89%) m.p., 245°–7° (dec.).

Calculated for $C_{29}H_{29}Cl_2N_3O_2 \cdot HCl$: C, 62.31; H, 5.41; N, 7.52. Found: C, 62.36; H, 5.31; N, 7.26.

EXAMPLE 9

3-[3-(4-phenyl-1-piperidyl)propyl]-5-(4-methoxyphenyl)-5-phenylhydantoin hydrochloride (TR 2985).

5-(4-methoxyphenyl)-5-phenylhydantoin (7.0 g, 0.025 mole) was added to sodium ethoxide (0.05 mole) in 350 ml of anhydrous ethanol. After warming for 30 minutes, 1-(3-chloropropyl)-4-phenylpiperidine. HCl (6.8 g, 0.025 mole) was added and the mixture was refluxed with stirring for 18 hours, filtered and diluted with $H_2O$. The solid was collected and recrystallized from aqueous 2-propanol.

Yield: 9 g (74.6%; m.p., 134°–6°. Calculated for $C_{30}H_{33}N_3O_3$: C, 74.51; H, 6.88; N, 8.69. Found: C, 73.55; H, 6.85; N, 8.48.

The free base (8.8 g, 0.018 mole) in hot anhydrous ethanol was converted to the HCl salt with $HCl_g$/2-propanol and ether. The salt was recrystallised from 2-propanol-methanol-ether.

Yield: 8.0 g (84.5%); m.p., 226°–7° (dec.). Calculated for $C_{30}H_{33}N_3O_3 \cdot HCl$: C, 69.29; H, 6.59; N, 8.08. Found: C, 69.16; H, 6.67; N, 7.94.

EXAMPLE 10

3-[3-(4-phenyl-1-piperidyl)propyl]-5,5-di(4-methoxyphenyl)hydantoin hydrochloride (TR 2986).

5,5-di(4-methoxyphenyl)hydantoin (7.8 g, 0.025 mole) was added to sodium ethoxide (0.05 mole) in 300 ml. of anhydrous ethanol and after warming for 30 minutes the solution was treated with 1-(3-chloropropyl)-4-phenylpiperidine · HCl (6.8 g, 0.025 mole). The mixture was refluxed with stirring for 18 hours, filtered and diluted with $H_2O$. The solid was recrystallized from aqueous ethanol.

Yield: 10.5 g (82%); m.p., 163°–4°.

Calculated for $C_{31}H_{35}N_3O_4$: C, 72.50; H, 6.87; N, 8.16. Found: C, 72.76; H, 6.70; N, 7.98.

The free base (10 g, 0.021 mole) in hot anhydrous ethanol was converted to the HCl salt with $HCl_g$/2-propanol and ether. The salt was recrystallized from methanol-ether.

Yield: 9.7 g (90.5%); m.p., 227°–8° (dec.).

Calculated for $C_{31}H_{35}N_3O_4 \cdot HCl$: C, 67.69; H, 6.60; N, 7.64. Found: C, 67.57; H, 6.73; N, 7.55.

EXAMPLE 11

3-[3-(4-phenyl-1-piperidyl)propyl]-5-(4-bromophenyl)-5-phenylhydantoin hydrochloride (TR 2987).

5-(4-bromophenyl)-5-phenylhydantoin (8.3 g, 0.025 mole) was added to sodium ethoxide (0.05 mole) in 300 ml of anhydrous ethanol and the solution was warmed for 30 minutes and 1-(3-chloropropyl)-4-phenylpiperidine · HCl (6.8 g, 0.025 mole) was added. The mixture was refluxed with stirring for 18 hours, filtered and diluted with $H_2O$. The solid was recrystallized from aqueous ethanol.

Yield: 11.6 g (87%); m.p., 178°–9°.

Calculated for $C_{29}H_{30}BrN_3O_2$: C, 65.41; H, 5.66; N, 7.89. Found: C, 65.42; N, 5.64; N, 8.16.

The free base (11 g, 0.020 mole) was converted to the HCl salt with $HCl_g$/2-propanol and recrystallized from 2-propanol-methanol-ether. Yield: 5.6 g (47.6%); m.p., 203°–6° (dec.).

Calculated for $C_{29}H_{30}BrN_3O_2 \cdot HCl$: C, 61.22; H, 5.49; N, 7.38. Found: C, 60.84; H, 5.36; N, 7.14.

EXAMPLE 12

3-[3-(4-phenyl-1-piperidyl)propyl]-5-phenyl-5-(4-tolyl) hydantoin maleate (TR 2993).

5-phenyl-5-(4-tolyl)hydantoin (6.6 g, 0.025 mole) was added to sodium ethoxide (0.05 mole) in 300 ml of anhydrous ethanol and the solution was warmed for 30 minutes and treated with 1-(3-chloropropyl)-4-phenylpiperidine · HCl (6.8 g, 0.025 mole). The mixture was refluxed with stirring for 18 hours, filtered and diluted with $H_2O$. The solid was recrystallized from aqueous ethanol.

Yield: 9.5 g (81%); m.p., 157°–9°.

Calculated for $C_{30}H_{33}N_3O_2$: C, 77.06; H, 7.11; N, 8.99. Found: C, 77.72; H, 7.15; N, 9.18.

The free base (9.5 g, 0.020 mole) was converted to the maleate salt with excess maleic acid in anhydrous ethanol, filtered and diluted with ether.

Yield: 4.3 g (36.3%); m.p., 216°–7° (dec.).

Calculated for $C_{30}H_{33}N_{33}O_2 \cdot C_4H_4O_4$: C, 69.97; H, 6.39; N, 7.20. Found: C, 70.00; H, 6.50; N, 6.96.

EXAMPLE 13

3-[3-(4-phenyl-1-piperidyl)propyl]-5,5-di(4-tolyl) hydantoin (TR 3001).

5,5-di(4-tolyl)hydantoin (7 g, 0.025 mole) was added to sodium ethoxide (0.05 mole) in 300 ml of anhydrous ethanol and the solution was warmed for 30 minutes and treated with 1-(3chloropropyl)-4-phenyl -piperidine · HCl (6.8 g, 0.025 mole). The mixture was refluxed for 18 hours with stirring, filtered and diluted with $H_2O$. The solid was recrystallized four times with aqueous ethanol and again with aqueous acetone.

Yield: 1.8 g (15%); m.p., 154°–5°.

Calculated for $C_{31}H_{35}N_3O_2$: C, 77.31; H, 7.32; N, 8.73. Found: C, 77.07; N, 7.32; N, 8.62.

EXAMPLE 14

3-[3-(4-phenyl-1-piperidyl)propyl]-5-(4-nitrophenyl) -5-phenylhydantoin (TR 3012).

5-(4-nitrophenyl)-5-phenyl -hydantoin (18 g, 0.06 mole) was added to sodium ethoxide (0.12 mole) in 500 ml of anhydrous ethanol and the solution was warmed and 1-(3-chloropropyl)-4-phenylpiperidine · HCl (16.6 g, 0.06 mole) was added. The mixture was refluxed with stirring for 18 hours, filtered and diluted with $H_2O$. The solid was recrystallized from aqueous-dimethylformamide-methanol.

Yield: 23 g (76.7%). A 5 g sample of the free base was twice recrystallized from aqueous-dimethylformamide-2-propanol-methanol and again from aqueous dioxane.

Yield: 1.8 g; m.p., 195°–6°.

Calculated for $C_{29}H_{30}N_4O_4$: C, 69.86; H, 6.06; N, 11.24. Found: C, 69.44; H, 6.08; N, 11.00.

EXAMPLE 15

3-[3-(4-phenyl-1-piperidyl)propyl]-5-(4-aminophenyl) -5-phenylhydantoin (TR 3021).

3-[3-(4-phenyl-1-piperidyl) propyl]-5-(4-nitrophenyl)-5-phenylhydantoin (17.5 g, 0.035 mole) in 200 ml of glacial acetic acid and 0.6 g of Pd/C (10%) was reduced on the Parr shaker. The theoretical amount of hydrogen was taken up. The mixture was filtered and concentrated. The concentrate in aqueous methanol was made basic with $NH_4OH$. The solid was recrystallized from aqueous dimethylformamide-methanol and twice from aqueous dioxane.

Yield: 10.5 g (64%); m.p., 215°–7°.

Calculated for $C_{29}H_{32}N_4O_2$: C, 74.33; H, 6.88; N, 11.96. Found: C, 74.25; H, 7.05; N, 11.73.

EXAMPLE 16

5,5-diphenyl-3-[2-hydroxy-3-(4-phenyl-1-piperidyl) propyl]-hydantoin oxalate (TR 3104).

A mixture of 5,5-diphenylhydantoin (10 g., 0.039 mole) and epichlorohydrin (10 g) in a solution of sodium ethoxide (0.039 mole) in 300 ml. of anhydrous EtOH was refluxed for 3 hours and concentrated. The concentrate was stirred in ether, filtered and concentrated. The concentrate and 4-phenylpiperidine (6.2 g, 0.039 mole) in 200 ml. of anhydrous EtOH were refluxed with stirring for 16 hours and concentrated to a viscous oil. The oil and oxalic acid (5 g) were dissolved in hot acetone and let stand at room temperature. The solid was collected and twice recrystallized from methanol-ether.

Yield: 8.5 g (39%); m.p., 119°–121° (dec.).

Calculated for $C_{29}H_{31}N_3O_3 \cdot C_2H_2O_4$: C, 66.54; H, 5.94; N, 7.51. Found: C, 67.08; H, 6.15; N, 7.47.

EXAMPLE 17

5,5-di(4-tolyl)-3-[2-hydroxy-3-(t-butylamino)propyl]-hydantoin hemioxalate (TR 3130).

5,5-di(4-tolyl)hydantoin (7 g, 0.025 mole), epichlorohydrin (10 g) and sodium ethoxide (0.025 mole) in 200 ml. of anhydrous EtOH were refluxed with stirring for 6 hours, filtered and concentrated to dryness in vacuo. The concentrate and t-butylamine (30 ml.) in 150 ml. of anhydrous EtOH were refluxed for 2 hours and concentrated. The concentrate was triturated in ether to solidify the oil and the solid was recrystallized from benzene.

Yield: 3.5 g (34.2%); m.p., 168°–9°.

Calculated for $C_{24}H_{31}N_3O_3$: C, 70.39; H, 7.63; N, 10.26. Found: C, 69.89; H, 8.16; N, 10.15.

The free base (3.5 g, 0.0085 mole) and oxalic acid (2 g) in MeOH were diluted with ether. The solid salt was recrystallized once from MeOH-ether and again from MeOH.

Yield: 1.5 g (38.7%); m.p. 283°–4° (dec.).

Calculated for $C_{24}H_{31}N_3O_3 \cdot \frac{1}{2} C_2H_2O_4$: C, 66.07; H, 7.09; N, 9.25. Found: C, 66.64; H, 7.12; N, 9.56.

EXAMPLE 18

3-[3-(4-hydroxy-4-phenyl-1-piperidyl)propyl]-5,5-di-(4-tolyl)hydantoin (TR 3163).

5,5-di-(4-tolyl)hydantoin (6 g, 0.02 mole) was added to a solution of sodium ethoxide (0.04 mole) in 350 ml of anhydrous ethanol and the solution was refluxed for 30 min. 1-(3-chloropropyl)-4-hydroxy-4-phenyl-piperidine · HCl (5.5 g, 0.02 mole) was added and the mixture was refluxed for 5 hours, then diluted with water. The solid was collected and recrystallized from aqueous ethanol.

Yield: 6 g (56.5%); m.p., 181°–2°.

Calculated for $C_{31}H_{35}N_3O_3$: C, 74.83; H, 7.09; N, 8.44. Found: C, 75.22; H, 7.29; N, 8.42.

The free base (5.7 g, 0.011 mole) was converted to the HCl salt with HCl (g) in 2-propanol-ethylacetate and recrystallized from 2-propanol-methanol-ethylacetate.

Yield: 4.1 g (67.2%); m.p., 230°–1° (dec.).

Calculated for $C_{31}H_{35}N_3O_3 \cdot HCl$: C, b 69.72; H, 6.80; N, 7.87. Found: C, 69.67; H, 6.77; N, 7.58.

EXAMPLE 19

Antiarrhythmic Activity

The antiarrhythmic activity of the compounds of this invention, specifically those enumerated in the *Summary* and presented as the above examples, was compared to that of diphenylhydantoin (I), 3-(3-diethylaminopropyl)-5,5-diphenylhydantoin (II), 3-[3-(1-piperidyl)-propyl]-5,5-diphenylhydantoin (III), and 3-(3-morpholinopropyl)-5,5-diphenylhydantoin (IV).

The tests compounds were administered to groups consisting of 5 mice in varying intraperitoneal doses. Ten minutes after administration of a given dose of a compound, a mouse was transferred to a covered 300 ml glass beaker which contained a wad of cotton saturated with about 20 ml of chloroform. The animal was observed closely and removed from the beaker immediately after respiratory arrest. The heart was quickly exposed by making an incision through the abdomen, diaphragm, thorax and pericardium for visual inspection of ventricular rate and rhythm. Ventricular contractions were counted for 30 seconds. According to the procedure reported by Lawson (J. Pharmacol. Exp. Therap., 160:22 [1968]), animals with a ventricular rate not exceeding 100 contractions during the 30 second observation period were considered protected. Results obtained with each dose were used to calculate the mean effective doses ($ED_{50}$) after the method of Litchfield and Wilcoxon (J. Pharmacol. Exp. Therap. 96: 99–113 [1949]). Deaths occurring after administration of each dose but before exposure to chloroform were noted in order to determine the minimum lethal dose for each compound. The results are shown in Table A.

In Table A, the compounds of this invention are listed by the arabic numeral assigned in the *Summary* and the above corresponding Example Number; the Roman numerals refer to the compounds so designated above in this Example and in the *Description of the Prior Art*.

Table A

| Compound | $ED_{50}$ (95% CL) mg/kg | MLD mg/kg | $MLD/ED_{50}$ |
|---|---|---|---|
| 1(MA 1586) | 16.4(8–35) | >160 | > 9.77 |
| 2(MA 1598) | 13.5(7–26) | 320 | 23.71 |
| 4(TR 2913) | 96.0(50–182) | >178 | > 1.85 |
| 5(TR 2916) | 5.8(3–11) | 31 | 5.35 |
| 6(TR 2921) | 9.4(6–15) | 100 | 10.62 |
| 8(TR 2984) | 75.0(39–142) | >178 | > 2.28 |
| 10(TR 2986) | 34.0(18–63) | >178 | > 5.24 |
| 11(TR 2987) | 33.5(22–52) | >100 | > 2.98 |
| 12(TR 2993) | 19.5(11–35) | >100 | > 5.13 |
| 13(TR 3001) | 4.5(2–12) | >100 | >22.20 |
| 14(TR 3012) | 10.5(5–21) | >100 | > 9.52 |
| 15(TR 3021) | 3.4(2–7) | >100 | >29.40 |
| 18(TR 3163) | 24.0(11–56) | >100 | > 4.17 |
| I | 394.0(296–529) | 1000 | 2.54 |
| II | 14.0(8–26) | 56 | 4.00 |
| III | 19.0(11–35) | 31 | 1.63 |
| IV | 76.0(35–163) | 178 | 2.34 |

$ED_{50}$ (95% CL) is the mean effective dose in mg/kg, intra-peritoneally; 95% CL is the confidence limits in mg/kg.
MLD is the Minimum Lethal Dose in mg/kg, intraperitoneally.
$MLD/ED_{50}$ is the Therapeutic Index calculated with Minimum Lethal Dose Data.

EXAMPLE 20

The effect of the compounds of this invention on the refractory period in the atrium was studied and compared to that hydantoin according to the procedure described by Dawes (Brit. J. Pharmacol., 1: 90, [1946]).

Guinea pig atria, suspended in an isolated organ chamber, were stimulated electrically at increasing frequencies while the resulting mechanical contractions were recorded. The minimum interval between two consecutive stimuli necessary for eliciting a mechanical response was determined before and after incubation with varying concentrations of the test compounds. The minimum interval thus determined is an indirect measure of the refractory period in the tissue, and a prolongation of this interval indicates an increased refractory period. From the increase in minimum interval observed with each concentration, the amount necessary for increasing the interval by 50 percent over control values ($EC_{50}$) was determined for each compound. As shown in Table B, the compounds of this invention (designated by the corresponding example number and arabic numeral assigned in the *Summary*) are more effective in prolonging the atrial refractory period (thus causing less cardiac depression) than the parent compound, diphenylhydantoin (designated as DPH).

Table B

| Compound | $EC_{50}$, mcg/ml |
|---|---|
| 1(MA 1586) | 4.4 |
| 2(MA 1598) | 1.1 |
| 4(TR 2913) | 5.7 |
| 5(TR 2916) | >10.0 |
| 6(TR 2921) | 1.5 |
| 8(TR 2984) | >10.0 |
| 10(TR 2986) | 6.4 |
| 11(TR 2987) | 4.0 |
| 12(TR 2993) | 4.8 |
| 13(TR 3001) | >10.0 |
| 14(TR 3012) | 8.3 |
| 15(TR 3021) | 3.7 |
| 18(TR 3163) | 1.9 |
| DPH (I) | 20.0 |

What is claimed is:

1. A method of treating a cardiac arrhythmia in a mammal which comprises:

administering to said mammal an antiarrhythmic effective amount of a compound selected from the group consisting of

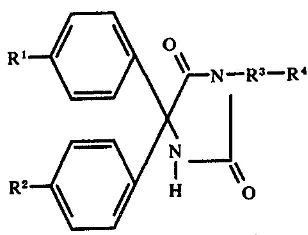

and a pharmacologically acceptable, nontoxic acid addition salt thereof, wherein:

$R^1$ and $R^2$ are selected from the group consisting of hydrogen, halogeno, loweralkyl of 1 to 3 carbon atoms, loweralkoxy of 1 to 3 carbon atoms, amino, and nitro;

$R^3$ is selected from the group consisting of ethylene and trimethylene, and $R^4$ is selected from the group consisting of 4-phenyl-1-piperidyl, 4-hydroxy-4-phenyl-1-piperidyl, 4-phenyl-1,2,3,6-tetrahydropyridyl, and 4-phenyl-1-piperazinyl.

2. A method as in claim 1 wherein said amount is from 5 to 500 mg/kg.

3. A method as in claim 1 wherein the compound is 3-[3-(4-phenyl-1-piperazinyl)propyl]-5,5-diphenylhydantoin maleate.

4. A method as in claim 1 wherein the compound is 3-[3-(4-phenyl-1-piperidyl)propyl]-5,5-diphenylhydantoin.

5. A method as in claim 1 wherein the compound is 3-[2-(4-phenyl-1-piperidyl)ethyl]-5,5-diphenylhydantoin ·HCl.

6. A method as in claim 1 wherein the compound is 5,5-diphenyl-3-[2-(4-phenyl-1,2,3,6-tetrahydropyridyl) ethyl]hydantoin · HCl.

7. A method as in claim 1 wherein the compound is 5,5-diphenyl-3-[3-(4-hydroxy-4-phenyl-1-piperidyl)-propyl]hydantcin · HCl.

8. A method as in claim 1 wherein the compound is 5,5-diphenyl-3-[2-(4-hydroxy-4-phenyl-1-piperidyl)ethyl]hydantoin · HCl.

9. A method as in claim 1 wherein the compound is 3-[3-(4-phenyl-1-piperidyl)propyl]-5,5-di(4-chlorophenyl) hydantoin · HCl.

10. A method as in claim 1 wherein the compound is 3-[3-(4-phenyl-1-piperidyl)propyl]-5-(4-methoxyphenyl)-5-phenylhydantoin · HCl.

11. A method as in claim 1 wherein the compound is 3-[3-(4-phenyl-1-piperidyl)propyl]-5,5-di(4-methoxyphenyl) hydantoin · HCl.

12. A method as in claim 1 wherein the compound is 3-[3-(4-phenyl-1-piperidyl)propyl]-5-(4-bromophenyl)-5 -phenylhydantoin · HCl.

13. A method as in claim 1 wherein the compound is 3-[3-(4-phenyl-1-piperidyl)propyl]-5-phenyl-5-(4-tolyl) hydantoin · maleate.

14. A method as in claim 1 wherein the compound is 3-[3-(4-phenyl-1-piperidyl)propyl)]-5,5-di(4-tolyl)-hydantoin.

15. A method as in claim 1 wherein the compound is 3-[3-(4-phenyl-1-piperidyl)propyl]-5-(4-nitrophenyl)-5-phenylhydantoin.

16. A method as in claim 1 wherein the compound is 3-[3-(4-phenyl-1-piperidyl)propyl]-5-(4-aminophenyl)-5-phenylhydantoin.

17. A method as in claim 1 wherein the compound is 3-[3-(4-hydroxy-4-phenyl-1-piperidyl)propyl]-5,5di(4-tolyl)hydantoin.

* * * * *